(12) United States Patent
Rugart

(10) Patent No.: US 11,793,548 B2
(45) Date of Patent: Oct. 24, 2023

(54) ORGAN ENCLOSURES FOR INHIBITING TUMOR INVASION AND DETECTING ORGAN PATHOLOGY

(71) Applicant: Eric S. Rugart, Haverford, PA (US)

(72) Inventor: Eric S. Rugart, Haverford, PA (US)

( * ) Notice: Subject to any disclaimer, the term of this patent is extended or adjusted under 35 U.S.C. 154(b) by 57 days.

(21) Appl. No.: 17/404,106

(22) Filed: Aug. 17, 2021

(65) Prior Publication Data
US 2022/0071660 A1 Mar. 10, 2022

Related U.S. Application Data

(63) Continuation of application No. 16/085,230, filed as application No. PCT/US2017/022644 on Mar. 16, 2017, now abandoned.
(Continued)

(51) Int. Cl.
*A61B 17/42* (2006.01)
*A61B 5/00* (2006.01)
(Continued)

(52) U.S. Cl.
CPC ............ *A61B 17/42* (2013.01); *A61B 5/02* (2013.01); *A61B 5/026* (2013.01); *A61B 5/055* (2013.01);
(Continued)

(58) Field of Classification Search
CPC .......... A61B 17/42; A61B 5/02; A61B 5/026; A61B 5/055; A61B 5/4325; A61B 10/02; A61B 17/00234; A61B 17/12031; A61B 17/12099; A61B 17/12131; A61B 90/39; A61B 17/12; A61B 2017/00088;
(Continued)

(56) References Cited

U.S. PATENT DOCUMENTS 4,983,177 A * 1/1991 Wolf .................... A61B 17/076
606/151
5,057,117 A * 10/1991 Atweh .................... A61M 1/02
606/151
(Continued)

FOREIGN PATENT DOCUMENTS

WO     2015075463     5/2015

OTHER PUBLICATIONS

Blood vessels and nerves: together or not? Commentary Philip J Hogg, Elspeth M McLachlan, vol. 360, Issue 9347, p. 1714, Nov. 30, 2002 (Year: 2002).*
(Continued)

*Primary Examiner* — Sunita Reddy
(74) *Attorney, Agent, or Firm* — William Bak; Kathleen D. Rigaut; Howson & Howson LLP

(57) ABSTRACT

An enclosure provides a prophylactic barrier that may be permeable to gases, hormones, proteins, and peritoneal fluid, but restrains tumor cells within the enclosure so as to inhibit ovarian cancer invasion of adjacent tissue, and increase the speed of diagnosis of ovarian dysplasia, including cancer. The enclosure includes one or more of fiducial markers, heat sensors, and blood flow reflectors, which may be imaged non-invasively in order to detect conditions or pathology affecting the ovary. The enclosure may also include an access port that permits sampling of the enclosure's contents to further aid in detecting or treating conditions or pathology affecting the ovary.

20 Claims, 9 Drawing Sheets

Related U.S. Application Data

(60) Provisional application No. 62/309,637, filed on Mar. 17, 2016.

(51) Int. Cl.

| | | |
|---|---|---|
| *A61B 10/02* | (2006.01) | |
| *A61K 35/44* | (2015.01) | |
| *A61B 5/055* | (2006.01) | |
| *A61B 5/02* | (2006.01) | |
| *A61K 35/35* | (2015.01) | |
| *A61L 31/14* | (2006.01) | |
| *A61L 31/00* | (2006.01) | |
| *A61B 17/00* | (2006.01) | |
| *A61F 2/04* | (2013.01) | |
| *A61B 90/00* | (2016.01) | |
| *A61B 5/026* | (2006.01) | |
| *A61B 17/12* | (2006.01) | |
| *A61F 2/00* | (2006.01) | |

(52) U.S. Cl.
CPC ............ *A61B 5/4325* (2013.01); *A61B 10/02* (2013.01); *A61B 17/00234* (2013.01); *A61B 17/12031* (2013.01); *A61B 17/12099* (2013.01); *A61B 17/12131* (2013.01); *A61B 90/39* (2016.02); *A61F 2/04* (2013.01); *A61K 35/35* (2013.01); *A61K 35/44* (2013.01); *A61L 31/005* (2013.01); *A61L 31/14* (2013.01); *A61B 17/12* (2013.01); *A61B 2017/00088* (2013.01); *A61B 2017/00287* (2013.01); *A61B 2017/00477* (2013.01); *A61B 2017/00876* (2013.01); *A61B 2017/00893* (2013.01); *A61B 2090/0816* (2016.02); *A61B 2090/3966* (2016.02); *A61F 2/0063* (2013.01)

(58) Field of Classification Search
CPC ........... A61B 2017/00287; A61B 2017/00477; A61B 2017/00876; A61B 2017/00893; A61B 2090/0816; A61B 2090/3966; A61F 2/04; A61F 2/0063; A61K 35/35; A61K 35/44; A61L 31/005; A61L 31/14
USPC ............................................... 600/37, 29–32
See application file for complete search history.

(56) References Cited

U.S. PATENT DOCUMENTS

| | | | |
|---|---|---|---|
| 5,186,711 A * | 2/1993 | Epstein | ............... A61B 90/00 600/37 |
| 5,279,539 A | 1/1994 | Bohan et al. | |
| 5,769,794 A | 6/1998 | Conlan et al. | |
| 6,165,121 A | 12/2000 | Alferness | |
| 6,332,466 B1 | 12/2001 | Yoon | |
| 2001/0038848 A1 | 11/2001 | Donda et al. | |
| 2003/0216611 A1 | 11/2003 | Vu | |
| 2004/0220608 A1 | 11/2004 | D'Aquanni et al. | |
| 2004/0243174 A1 | 12/2004 | Ackerman et al. | |
| 2005/0137677 A1 | 6/2005 | Rush | |
| 2005/0149173 A1 | 7/2005 | Hunter et al. | |
| 2005/0159774 A1 | 7/2005 | Belef | |
| 2005/0234557 A1 | 10/2005 | Lambrecht et al. | |
| 2006/0224234 A1 | 10/2006 | Jayaraman | |
| 2007/0154515 A1 | 7/2007 | Johnson et al. | |
| 2007/0207186 A1 | 9/2007 | Scanlon et al. | |
| 2007/0293932 A1 | 12/2007 | Zilla et al. | |
| 2009/0024152 A1 | 1/2009 | Boyden et al. | |
| 2009/0192510 A1 | 7/2009 | Bahney | |
| 2009/0214615 A1 | 8/2009 | Zhao | |
| 2009/0254106 A1 * | 10/2009 | Forsell | ............... A61M 60/148 607/3 |
| 2010/0070019 A1 | 3/2010 | Shalev | |
| 2010/0256579 A1 | 10/2010 | Billsbury | |
| 2010/0292774 A1 | 11/2010 | Shalev | |
| 2012/0035414 A1 * | 2/2012 | Santillan | ............ A61B 17/0218 600/37 |
| 2012/0059394 A1 | 3/2012 | Brenner et al. | |
| 2013/0030408 A1 | 1/2013 | Piferi et al. | |
| 2014/0107406 A1 | 4/2014 | Hjelle et al. | |
| 2014/0121677 A1 | 5/2014 | Clancy et al. | |
| 2014/0236168 A1 * | 8/2014 | Shibley | ............. A61B 17/0218 606/114 |
| 2014/0243580 A1 | 8/2014 | Isham | |
| 2014/0330285 A1 * | 11/2014 | Rosenblatt | ....... A61B 17/00234 606/114 |
| 2015/0196369 A1 | 7/2015 | Glossop | |
| 2015/0297316 A1 | 10/2015 | Grinstaff et al. | |
| 2016/0144074 A1 * | 5/2016 | Matheny | ................ A61L 27/34 424/94.1 |
| 2016/0242751 A1 | 8/2016 | Bonadio et al. | |
| 2016/0249934 A1 | 9/2016 | Hewitt et al. | |
| 2016/0296293 A1 | 10/2016 | Gill et al. | |
| 2017/0049427 A1 | 2/2017 | Do et al. | |
| 2018/0008250 A1 * | 1/2018 | Joseph | ............ A61B 17/00234 |

OTHER PUBLICATIONS

IN 2338/CHE/2013 (Sree Chitra Tirunal Institute For Medical Sciences and Technology), 2015.

* cited by examiner

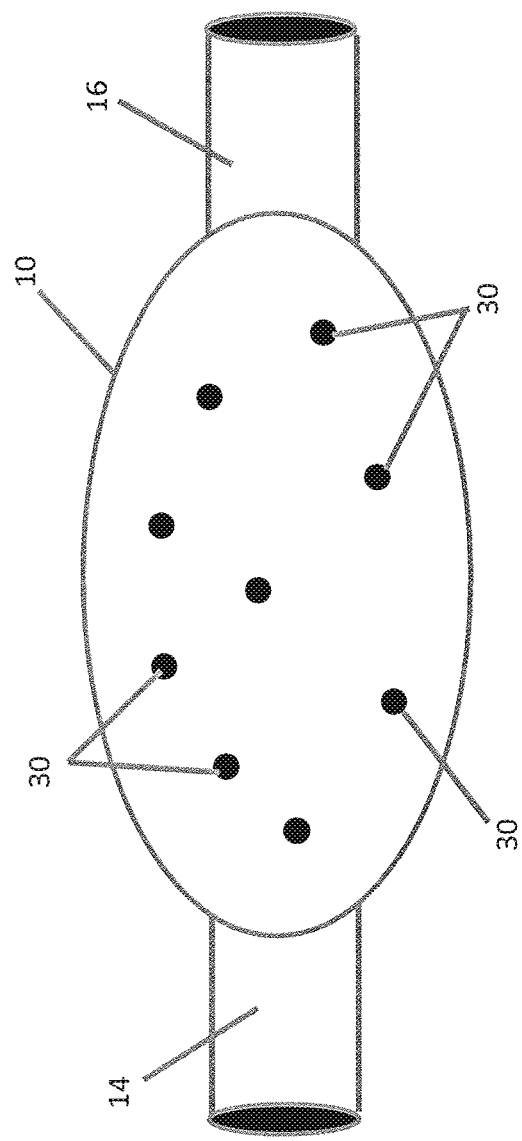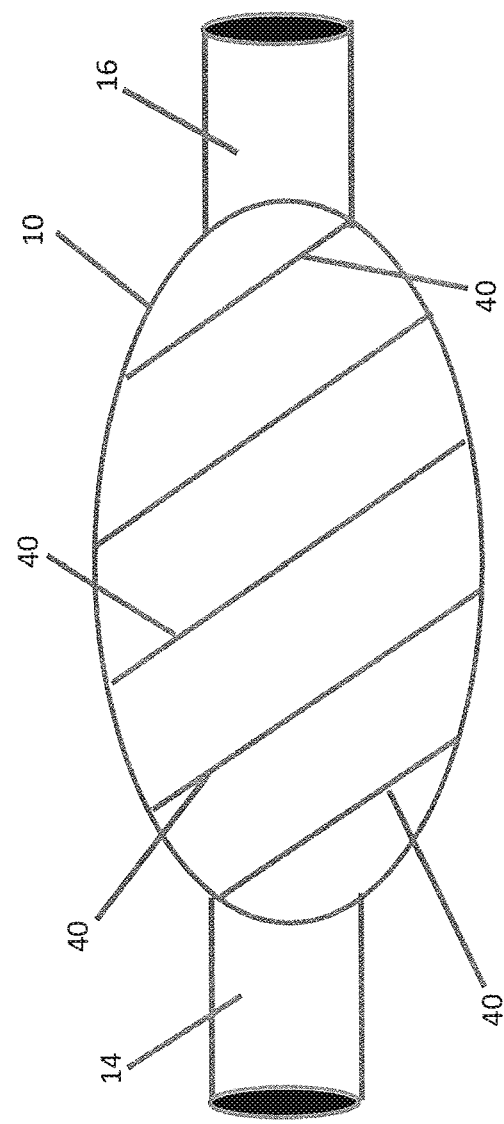

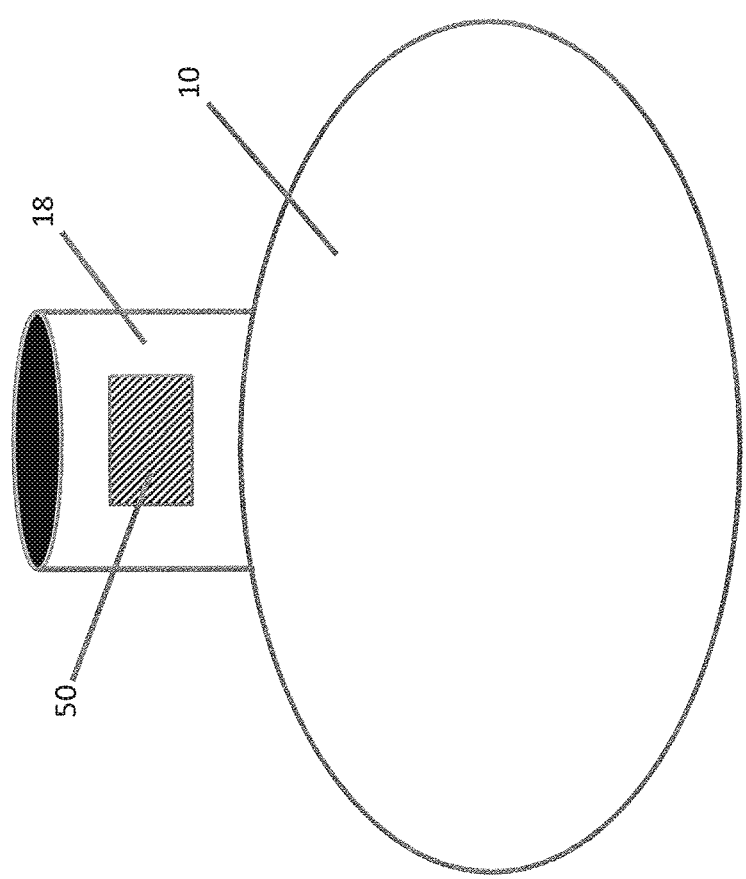

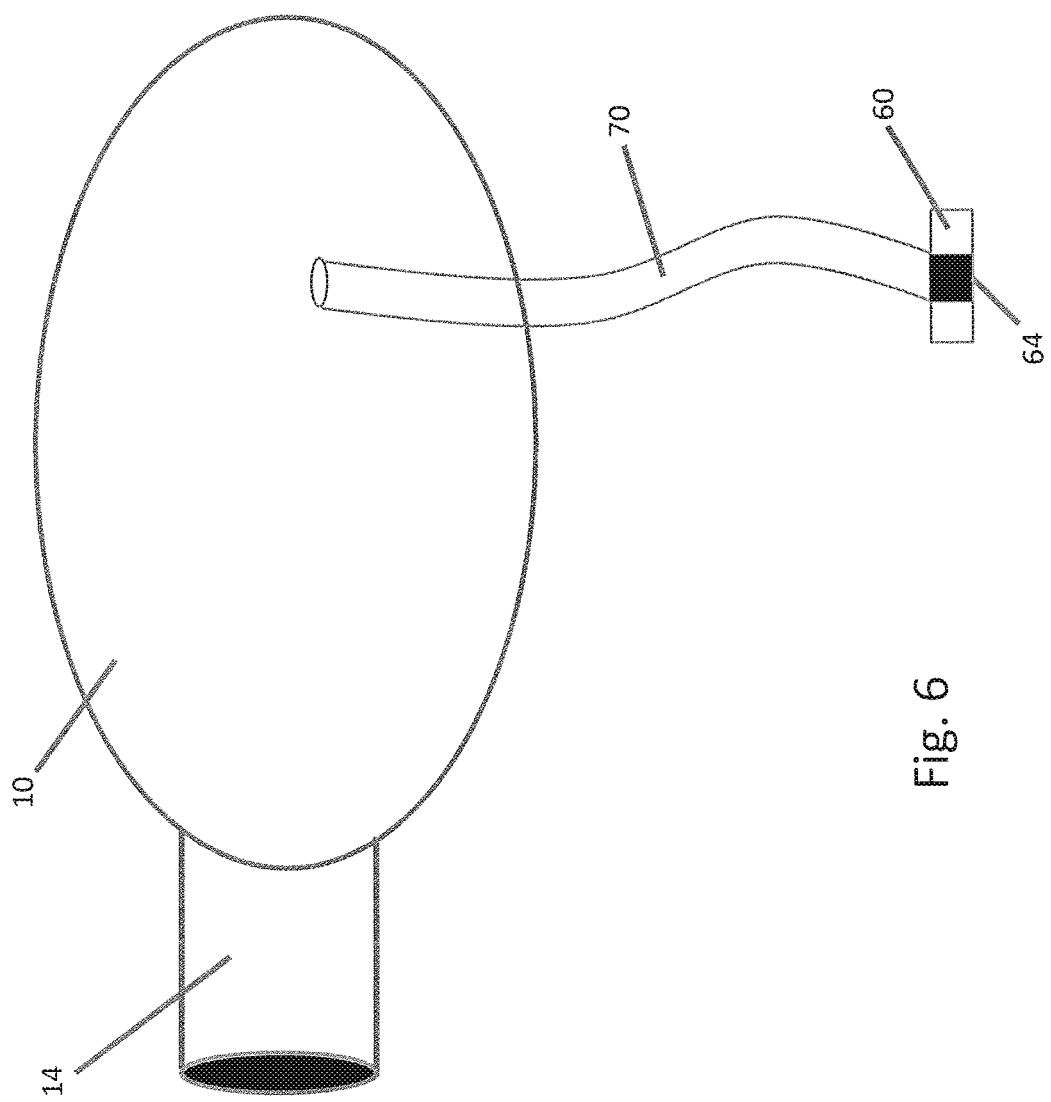

ORGAN ENCLOSURES FOR INHIBITING TUMOR INVASION AND DETECTING ORGAN PATHOLOGY

CROSS-REFERENCE TO RELATED APPLICATIONS

This application claims priority to U.S. provisional application Ser. No. 62/309,637 filed Mar. 17, 2016, which is incorporated herein by reference in its entirety.

FIELD

The disclosure relates to implantable devices for enclosing an organ, such as an ovary, in order to inhibit tumor cells, such as ovarian tumor cells, from invading adjacent tissue. The implantable enclosures are useful, for example, for preserving one or both ovaries during a hysterectomy procedure, and for inhibiting invasive metastasis of ovarian tumors.

BACKGROUND

Various publications, including patents, published applications, technical articles and scholarly articles are cited throughout the specification. Each of these cited publications is incorporated by reference herein, in its entirety and for all purposes.

There are over 100 recognized human cancer types, of which three main categories effect the ovary: Epithelial Tumors (surface)=90% of malignant ovarian tumors; Germ Cell Tumors=5% of malignancies; and Metastatic Tumors (Krukenberg tumors originating elsewhere in body)=5% of malignancies. What is constant in these presentations is that each causes a cascade of events which may be observed. In the pre-cancerous stage, the ovary displays dysplasia, changes in surface topography and characteristics (e.g., lesions that may present as unusually hard or soft areas of tissue, discolorations unrelated to ovulation, etc.). To aid oncogenesis (progression to full blown cancer) increased blood supply is demanded from the organ, increasing its metabolism to accommodate the demand for new vasculature formation (angiogenesis) and an inevitable inflammation of surrounding tissue in response to tumor formation.

The most consistent symptoms of ovarian cancer are morphologic (e.g., dysplasia); it distorts the ovary's shape and swells the ovary, often to many times its base-line size. This growth is often unaccompanied by discomfort or pain, as the ovary is designed to expand painlessly to aid procreation (ovulation is normally accompanied by ovarian expansion).

Ovarian cancer persists undetected because the organ itself is difficult to image. Even methods employing extreme ionizing radiation, such as CT and PET scans do not accurately indicate ovarian tissue, even in the metastatic stages of ovarian cancer. Physicians do not employ such dangerous imaging modalities for a routine annual pelvic exam but do employ ultrasound sonography, itself a far less effective tool for detecting ovarian tissue than is CT or PET scanning.

Pain is the overwhelming complaint driving the initial clinical presentation of women with ovarian cancer. One problem is that pain caused by ovarian cancer is usually the result of abdominal distensions, ascites, bloating, cramping and intestinal blockage; all signs of mature, metastatic ovarian cancer at stage 3 or 4 development. Mature metastatic ovarian cancer is the typical stage at diagnosis of ovarian cancer and the result is dramatically poorer 5 year survival outcomes than does early stage 1 or pre-cancerous diagnosis.

Hysterectomy procedures are quite common, with about 650,000 such procedures performed yearly in the United States alone. The procedure, which involves surgical removal of all or a portion of the uterus, is generally elective. Hysterectomy procedures are indicated due to pelvic cancers in only 90% of all U.S. history (Hx).

As a form of defensive medicine (i.e., medical practices performed mainly to reduce the legal liability of the medical professionals) arising from a perceived risk of ovarian cancer, an elective bilateral oophorectomy (EBO) is commonly performed concomitant with the hysterectomy procedure. The EBO involves the removal of both ovaries. An elective bilateral salpingo-oophprectomy (EBSO) includes fallopian tube removal in addition to the uterus, during the hysterectomy.

The most recent industry study determined EBO is performed in 69% of open hysterectomies, 60% of laparoscopic hysterectomies, and 30% of vaginal hysterectomies for a total of 62% of all hysterectomies. It is estimated that EBO results in two to four times as many deaths as ovarian cancer itself, taking into account the association between oophorectomy and decreased overall health and life expectancy, including contributing to the development of heart disease, a diminished cognitive capacity, and osteoporosis. In fact, the American Medical Association (AMA) and the American Congress of Obstetricians and Gynecologists (ACOG) have conducted educational programs detailing patient harm due to defensive medical practices and labeled EBO a "practice of concern" to their membership. Nevertheless, the removal of otherwise healthy ovaries during hysterectomy procedures persists, as the perceived risk of ovarian cancer appears to outweigh the actual risks that materialize following EBO.

For its part, ovarian cancer is estimated to cause about 15,500 deaths per year, with mean age of detection around age 65 and death around age 72. Ovarian cancer grows rapidly and metastasizes relatively early. Screening methods for ovarian cancer are somewhat deficient, at least as concerns early detection.

Ovarian cancers typically do not disseminate/metastasize via the blood or lymph. Rather, the ovarian cancer usually initially spreads via direct invasion of adjacent tissue. Accordingly, it may be possible in some instances to contain ovarian cancer to the ovary, thereby reducing the downstream pathologic risks, and advance indications such as pain that accelerate clinical presentation. This, in turn, should reduce the need for defensive ovary removal.

SUMMARY

The present disclosure provides enclosures comprising: a biotextile, a medical textile, or both a biotextile and a medical textile; a suspensory ligament sleeve, an ovarian ligament sleeve, or both a suspensory ligament sleeve and an ovarian ligament sleeve; and a plurality of fiducial markers; wherein the enclosure has an elasticity that allows the enclosure to expand in size; and wherein the biotextile, medical textile, or both the biotextile and the medical textile inhibit the passage of live cells out from the enclosure.

The present disclosure also provides methods for inhibiting ovarian tumor cell invasion of tissue adjacent to the ovary, comprising enclosing one or both ovaries in a subject in need thereof within the enclosure according to any one of the embodiments disclosed herein, thereby inhibiting ovarian tumor cell invasion of tissue adjacent to one or both ovaries in the subject.

The present disclosure also provides methods for treating a pathologic condition of the ovary, comprising detecting a change in the location, position, or spacing of the plurality of fiducial markers of the enclosure according to any one of the embodiments disclosed herein which has been implanted in the body of a subject, obtaining a sample of the internal contents of the enclosure, and determining the type of pathologic condition of the ovary based on testing conducted on the sample, and treating the pathologic condition.

BRIEF DESCRIPTION OF THE DRAWINGS

The present disclosure can be understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawing are the following figures.

FIG. 4A shows an example of an ovarian enclosure having a plurality of fiducial markers.

FIG. 4B shows an example of an ovarian enclosure having a plurality of heat sensing markers.

FIG. 4C shows an example of an ovarian enclosure having a blood flow reflector.

FIG. 6 shows an example of an ovarian enclosure with an access port and a tube that is operably connected to the ovarian enclosure on the proximal side of the tube and to the access port on the distal side of the tube.

DETAILED DESCRIPTION

Various terms relating to embodiments of the disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" or "patient" are used interchangeably and refer to any animal. Mammals are suitable, and include companion and farm mammals, as well as rodents, including mice, rabbits, and rats, and other rodents. Primates are suitable, and human beings are exemplary.

The organ enclosures described herein are adapted and configured to at least partially or completely encircle an organ of a mammal such that organ cells remain adjacent to the organ or within one or more layers of the enclosure. As a result, produced organ cells remain adjacent to the organ or within the enclosure, thereby mitigating the admission of produced organ cells into the surrounding anatomical space. In some embodiments, an organ enclosure may include one or more anchoring or fixation elements to secure the enclosure to one or more of a layer of an organ, a ligament of an organ, an artery or vein associated with an organ or other structure associated with an organ.

The present disclosure provides organ enclosures that comprise a biotextile, a medical textile, or both a biotextile and a medical textile. The enclosure inhibits the passage of live organ cells (e.g., cancer cells) out from the enclosure and has an elasticity that allows the enclosure to expand in size. The enclosure may further inhibit surgical adhesions. The enclosure comprises one or more ligament sleeves, and an optional port for accessing the internal contents of the enclosure. The enclosure may further comprise one or more blood vessel sleeves. The enclosure may further comprise a plurality of fiducial markers, which may be imaged or visualized by one or more of ultrasonic imaging, magnetic resonance imaging, or radiographic imaging, such as x-ray or tomography. The enclosure may comprise a single layer or a plurality of layers. The enclosure may comprise an outer layer and an inner layer, and a space between the outer layer and the inner layer capable of trapping live organ cells.

The organ enclosures described herein can be designed for any organ. In some embodiments, the organ enclosure is an ovarian enclosure. In some embodiments, the organ enclosure is a kidney enclosure, a pancreas enclosure, lobes of the lung enclosure, a liver enclosure, a spleen enclosure, a prostate gland enclosure, a stomach enclosure, an appendix enclosure, a gall bladder enclosure, a urinary bladder enclosure, or a testicle enclosure.

Figure 1:
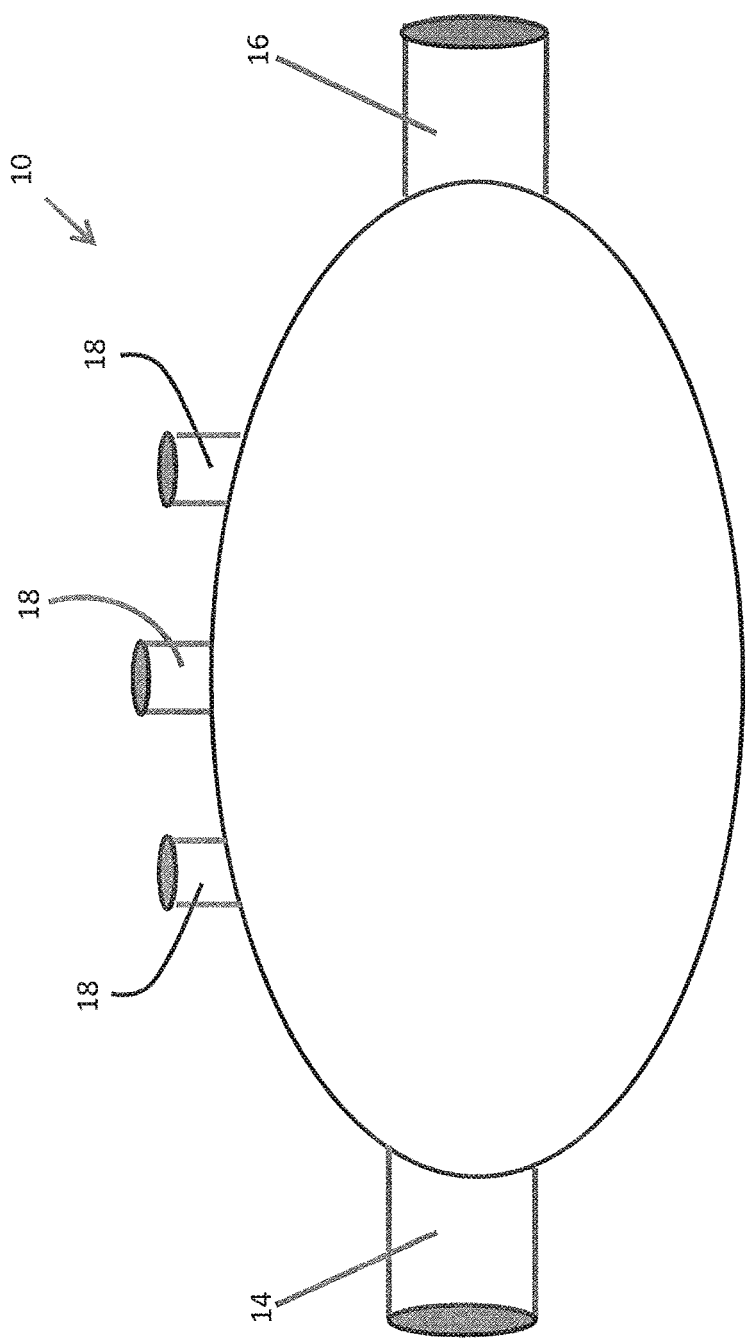
FIG. 1 shows an example of an ovarian enclosure, which comprises one or more sleeves for enclosing at least a portion of one or more of the suspensory ligament, the ovarian ligament, or blood vessels supplying the ovary.

Referring now to the drawings, in which like reference numbers refer to like elements throughout the various figures that comprise the drawings, FIG. 1 shows a perspective view of a first embodiment of an organ enclosure. Although the drawings refer to an ovarian enclosure 10, the drawings equally apply to any organ enclosure. The ovarian enclosure 10 is biocompatible, and comprises a biotextile or medical textile suitable for long-term, semi-permanent, or permanent implantation within the body. Such biotextiles and medical textiles may comprise a natural or synthetic material, or a combination of natural and synthetic materials. The ovarian enclosure 10 may serve a prophylactic role once implanted.

Biotextiles include materials obtained or derived from living tissue, including the stroma and extracellular matrix. Biotextiles may be obtained or derived from any source tissue including, but not limited to, skin, pericardium, peritoneum, small or large intestine, stomach, and other suitable tissues. Biotextiles may comprise one or more of autograft tissue, allograft tissue, or xenograft tissue. In some embodiments, the biotextile may comprise xenograft extracellular matrix. For xenograft tissue, the animal source may be a pig, cow, sheep, or non-human primate. For allograft tissue, suitable live donors or cadavers may be used as the source. Biotextiles can be non-immunogenic, and can be devoid of growth factors and other factors that promote cellular invasion and vascularization, since the ovarian enclosure 10 is not intended to function in the same capacity as a tissue repair scaffold.

Medical textiles include biocompatible synthetic materials. Examples of synthetic materials include, but are not limited to, polypropylene, polyethylene, polyvinyl chloride, polyurethane, polyethylene terephthalate, poly-L-lactide, poly-DL-lactide, polyglycolic acid, poly(lactic-co-glycolic acid), polydioxanone, polytetrafluoroethylene, nylon, and copolymers thereof, and silicone rubbers or neoprene rubbers, metals and foils, as well as natural polymers such as collagen, gelatin, elastin keratin, actin, and polysaccharides such as cellulose, alginate, fibrin, amylose, chitin, dextran, and glycosaminoglycan. Any combination of one or more of such materials may be used. In some embodiments, the medical textile comprises polypropylene. In some embodiments, the medical textile comprises polytetrafluoroethylene. In some embodiments, the medical textile comprises a silicone rubber. In some embodiments, the medical textile comprises a neoprene rubber. The enclosure may also comprise any combination of polypropylene, polytetrafluoroethylene, silicone rubber, or neoprene rubber.

In some embodiments, biotextiles and medical textiles may also be used in combination. The biotextile or the medical textile may also comprise a biocompatible film.

In some embodiments, the enclosure 10 comprises a bioresorbable material (e.g., biotextile or medical textile) in combination with a non-resorbable material (e.g., biotextile or medical textile), which may help to inhibit the formation of adhesions from the surgical procedure. Such a material may be resorbed by the body after a period of time, though the non-resorbable material remains, keeping the integrity and functionality of the enclosure 10 intact.

The biomedical and/or medical textiles may comprise any suitable form, including a mesh, weave, non-woven, sponge, foam, fabric, sheet, or film. The ovarian enclosure 10 may comprise one or more layers of biotextiles, medical textiles, or both biotextiles and medical textiles. In some embodiments, the ovarian enclosure 10 comprises a single layer. In some embodiments, the ovarian enclosure 10 comprises two layers, which may include a space in between. Each layer may comprise any suitable thickness.

The layers of the ovarian enclosure 10 can be impermeable or porous, albeit selectively permeable. In some embodiments, the pore sizes are no less than about 100 picometers. In some embodiments, the pore sizes are no greater than about 1.0 micron. In some embodiments, the pore sizes are from about 100 picometers to about 1.0 micron, from about 100 picometers to about 0.1 micron, or from about 100 picometers to about 0.01 micron. Thus, biologic fluids (e.g., blood and abdominal fluid), hormones (e.g., follicle-stimulating hormone (FSH)), gases (e.g., oxygen and carbon dioxide), and waste materials (including cellular debris) may freely pass through the layers of the ovarian enclosure 10, such that the ovary may be properly perfused. However, live, intact ovary cells, including ovum, are prevented from passing through the layers of the ovarian enclosure 10. In some embodiments of a multiple layered enclosure 10, ovary cells or ovum may pass through the inner layer that is adjacent to the ovary itself, but may not pass through the outer layer of the enclosure 10—for example, such cells remain trapped in a lumen or space located between the inner and outer layers. Thus, ovarian tumor cells are prevented from passing through the ovarian enclosure 10 once the enclosure 10 is properly implanted within the body.

The ovarian enclosure 10 may be in the form of a capsule, bag, pouch, cloche, sack, wrap, envelope, or other suitable container. The ovarian enclosure 10 may be rigid or flexible, and may also be pliable or elastic, sufficient to expand to a point in the event that ovarian cancer cells accumulate within the enclosure 10. In some embodiments, the ovarian enclosure 10 is flexible. In some embodiments, the ovarian enclosure 10 may have any suitable size, or length, width, and height dimensions. In some embodiments, the ovarian enclosure 10 is tailored to a patient's particular ovary size.

In some embodiments, the ovarian enclosure 10 sufficiently flexes or moves to accommodate patient movement and load forces, such that the enclosure 10, once implanted, does not cause pain from the patient bending or torqueing. In some embodiments, the ovarian enclosure 10 does not induce pain from intercourse. In some embodiments, the ovarian enclosure 10 has sufficient tensile strength such that it does not tear or break from patient movement or related stress.

In some embodiments, however, the ovarian enclosure 10 may be designed to be limited in its flexibility, such that it does not infinitely stretch in order to prevent pain felt by the subject. In cancerous states, although an ovary may be enlarged, it is often not painful to the subject. In such embodiments where the ovarian enclosure 10 is designed to be limited in its flexibility, pain may be perceived by the subject having an enlarged, and possibly cancerous, ovary. Thus, an ovarian enclosure that is designed to be limited in its flexibility may aid in the diagnosis of a disease state whereby the subject perceives pain in the presence of the ovarian enclosure who may not otherwise perceive the pain in the absence of the ovarian enclosure. In some embodiments, the ovarian enclosure may expand up to 75%, up to 80%, up to 85%, up to 90%, up to 95%, up to 100% (which would be a doubling in its expansion), up to 105%, up to 110%, up to 115%, up to 120%, up to 125%, or up to 130%, thus allowing for expansion while still providing sufficient restriction to allow the subject to perceive pain.

In pliable or elastic embodiments, the material of the ovarian enclosure 10 may expand about an additional 50% in size, though this expansion does not expand the pore size/porosity sufficiently to allow ovary cells to pass though. The ovarian enclosure 10 may expand from about 1% to about 50% in size, from about 1% to about 35%, from about 1% to about 25%, from about 1% to about 20%, from about 1% to about 15%, from about 1% to about 10%, from about 1% to about 5%, from about 5% to about 50%, from about 5% to about 25%, from about 5% to about 20%, from about 5% to about 15%, from about 5% to about 10%, from about 10% to about 50%, from about 10% to about 40%, from about 10% to about 30%, from about 10% to about 20%, from about 10% to about 15% in size, from about 20% to about 50%, from about 20% to about 40%, from about 20% to about 35%, from about 25% to about 50%, from about 25% to about 40%, from about 30% to about 50%, or from about 30% to about 40% in size. In some embodiments, the enclosure may expand up to about 50% in size. In some embodiments, the enclosure may expand up to about 33% in size. In some embodiments, the enclosure may expand up to about 25% in size. In some embodiments, the enclosure may expand up to about 10% in size. In some embodiments, the enclosure may expand more than 50% in size. In some embodiments, the enclosure may expand up to 55% in size, up to 55% in size, up to 60% in size, up to 65% in size, up to 70% in size, up to 75% in size, up to 80% in size, up to 85% in size, up to 90% in size, up to 95% in size, up to 100% in size, up to 105% in size, up to 110% in size, up to 115% in size, up to 120% in size, up to 125% in size, up to 130% in size, up to 135% in size, up to 140% in size, up to 145% in size, up to 150% in size, up to 155% in size, up to 160% in size, up to 165% in size, up to 170% in size, up to 175% in size, up to 180° % a in size, up to 185% in size, up to 190% in size, up to 195% in size, or up to 200% in size.

In some embodiments, the organ enclosure has non-adherent properties such that once implanted, the enclosure does not adhere to adjacent tissue. In some embodiments, the ovarian enclosure 10 also does not promote cellular invasion or vascularization, and does not promote fibrosis or desmoplasia. In some embodiments, though biocompatible, the ovarian enclosure 10 is biologically inert. In some embodiments, the means of affixing the organ enclosure does not impede or interfere with the organ vasculature. In some embodiments, the means of affixing the ovarian enclosure does not impede or interfere with the ovarian vasculature.

Prior to a hysterectomy or other surgical alteration of the female reproductive system, the ovary is ordinarily supported in place by a suspensory ligament, which attaches the ovary to the pelvic sidewall, an ovarian ligament, which attaches the ovary to the uterus, and a broad ligament, which supports the ovary (via the mesovarium) and its vasculature. In a typical ovary-sparing hysterectomy procedure, the ovarian ligament connection is severed, and the broad ligament connection is modified. The suspensory ligament, however remains.

Accordingly, in some embodiments, the ovarian enclosure 10 includes a suspensory ligament sleeve 14, and may further include an ovarian ligament sleeve 16, and may further include one or more vasculature sleeves 18 (see, FIG. 1). The suspensory ligament sleeve 14, the ovarian ligament sleeve 16, and the one or more vasculature sleeves 18 extend from the main body of the enclosure 10, and enclose at least a portion of each ligament or blood vessels (arteries and veins) that supply the ovary. The suspensory ligament sleeve 14 and the ovarian ligament sleeve 16 may have any length suitable to ensure that cancerous ovary cells that cannot invade via a ligament. The one or more vasculature sleeves 18 may also have any suitable length.

Figure 2:
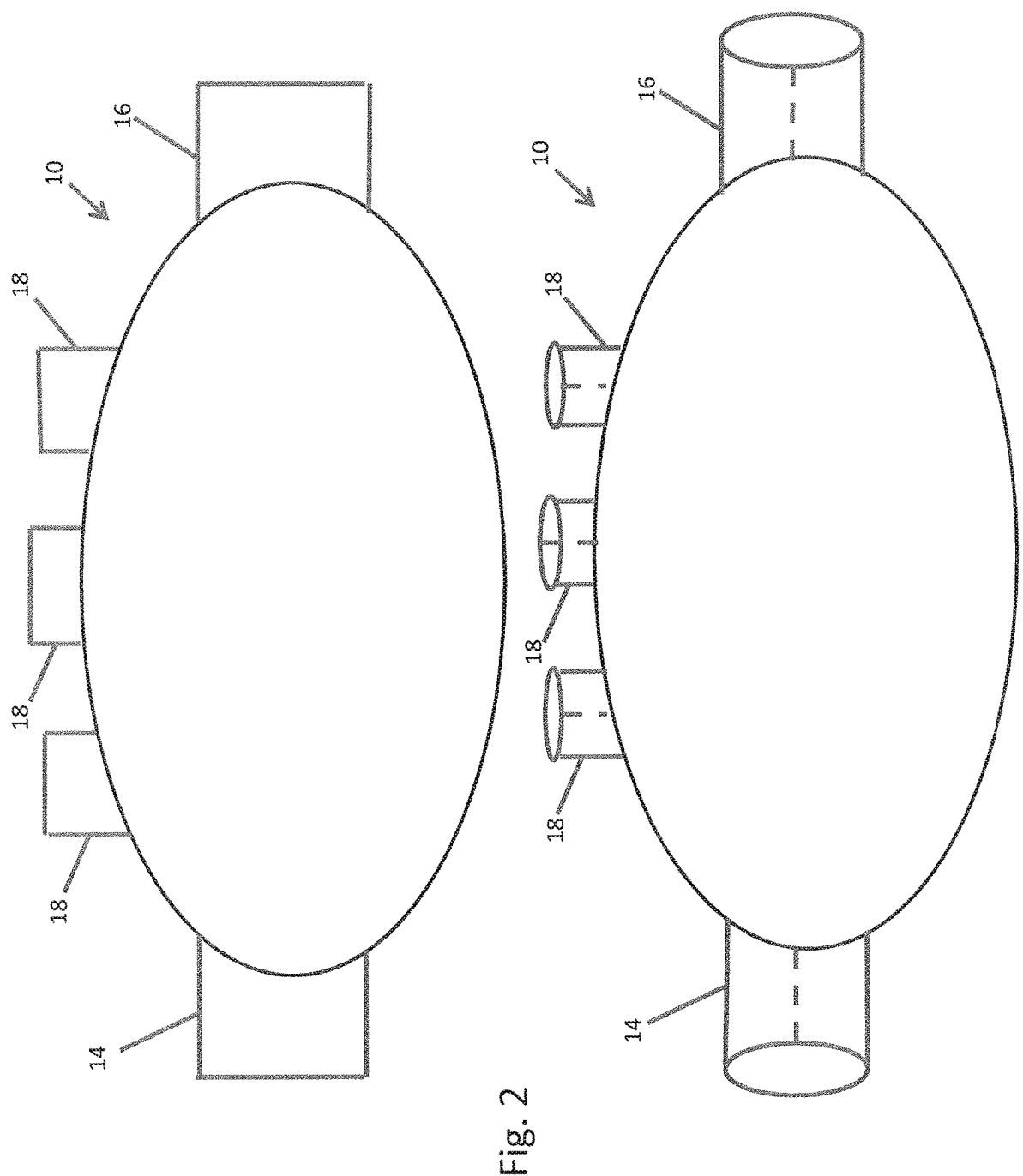
FIG. 2 shows an example of an open and closed configuration of ligament and blood vessel sleeves of the ovarian enclosure.

As the suspensory ligament, ovarian ligament (if retained), and blood vessels remain attached to the body opposite their connection to the ovary, the suspensory ligament sleeve 14, the ovarian ligament sleeve 16, and the one or more vasculature sleeves 18 may, in some embodiments, be open before and during the initial stages of the procedure to implant the ovarian enclosure 10, but then closed around their respective ligament or blood vessels later during the implantation procedure (see, FIG. 2). To close the suspensory ligament sleeve 14, the ovarian ligament sleeve 16, and the one or more vasculature sleeves 18, each sleeve 14, 16, 18 may be sewn/sutured, glued, tied, banded, stapled, heat-sealed/melt-sealed, clamped, or otherwise sealed around their respective ligament or blood vessels.

In some embodiments, for example, where the ovarian ligament is surgically cut from the ovary, the ovarian enclosure 10 may include only a suspensory ligament sleeve 14, and be otherwise sealed all the way around. In this manner, the enclosure is placed around the ovary, with one or more blood vessels and the suspensory ligament placed into and through the suspensory ligament sleeve 14, upon which the sleeve 14 may be sewn/sutured, glued, tied, banded, stapled, heat-sealed/melt-sealed, clamped, or otherwise sealed around the suspensory ligament and blood vessels.

Figure 3A:
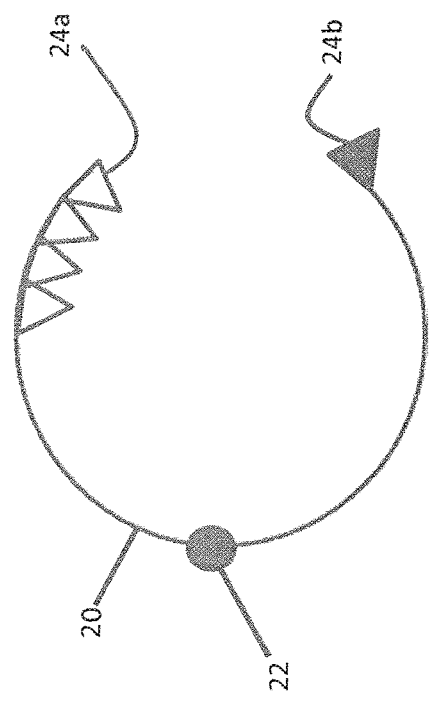
FIG. 3A shows an example of a clamp for securing a sleeve of the ovarian enclosure to a ligament or a blood vessel.
Figure 3B:
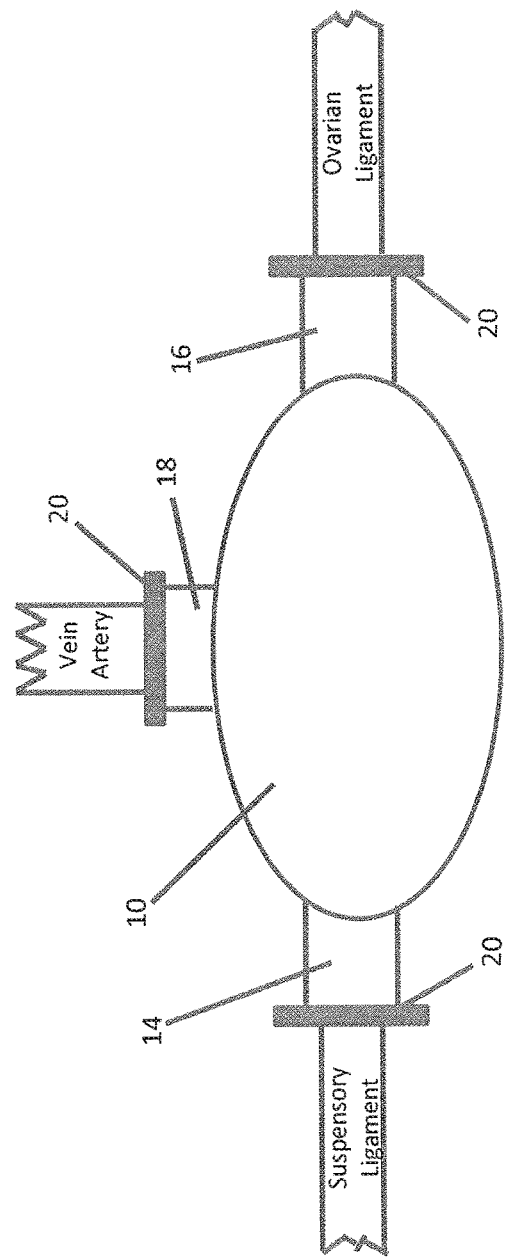
FIG. 3B shows an example of a plurality of clamps used to secure the sleeve to ligaments and blood vessels.

In some embodiments, the suspensory ligament sleeve 14, the ovarian ligament sleeve 16, and the one or more vasculature sleeves 18 are sealed around their respective ligament or blood vessels with a clamp 20, for example, as shown in FIG. 3A. The clamp 20 may comprise a hinge 22, as well as to ends 24a and 24b that surround an opening. Thus, the clamp 20 may be placed over top of the suspensory ligament sleeve 14, the ovarian ligament sleeve 16, or the one or more vasculature sleeves 18, then closed by squeezing about the hinge, with the ends 24a and 24b mating/locking/latching together. The ends 24a and 24b may comprise a ratchet or teeth and a pawl/lever, which allow the clamp 20 to close to accommodate larger or smaller ligaments or blood vessels. A plurality of clamps 20 may be used in conjunction with securing the ovarian enclosure 10 to the ovary (see, FIG. 3B).

Thus, in some embodiments, the enclosure further comprises one or more clamps. For example, the enclosure may further comprise a first clamp for securing the suspensory ligament sleeve to the suspensory ligament connected to the ovary. The enclosure may further comprise one or more second clamps for securing the one or more blood vessel sleeves to blood vessels connected to the ovary. The enclosure may further comprise a first clamp for securing the suspensory ligament sleeve to the suspensory ligament connected to the ovary and a third clamp for securing the ovarian ligament sleeve to the ovarian ligament connected to the ovary. The enclosure may further comprise one or more second clamps for securing the one or more blood vessel sleeves to blood vessels connected to the ovary. Any of the first clamp, second clamp, or third clamp may comprise a hinge, a first end, and a second end, and the first end and second end are capable of locking together. In some embodiments, the attachment can be carried out without using clamps. For example, a biocompatible glue, which may be approved for internal use, may be used. In some embodiments, a suture or barb, or other means, such as friction or a deformation made permanent (such as a foil), or a process that cures after attachment, such as a silicon gel, may be used.

Thus, the ovarian enclosure 10 is implanted and is attached to at least the suspensory ligament, as well as blood vessels and, in some cases, to the ovarian ligament. In some embodiments, the enclosure 10 envelopes, but is not affixed to the ovary itself. In some embodiments, however, the enclosure 10 is affixed directly to one or more surfaces of the ovary, for example, via an adhesive, or via a form of shrink-wrapping or kinetic distortion, e.g., a foil-like wrap. In some embodiments, no portion of the ovarian enclosure adheres to the surface of the ovary. In some embodiments, a portion of the ovarian enclosure adheres to the surface of the ovary.

The ovarian enclosure 10 is surgically implanted, and is suitable for implantation via an open/laparotomy type procedure, or via a laparoscopic procedure. The ovarian enclosure 10, and its sleeves 14, 16, 18 may be applied to their respective anatomical structure via unrolling, wrapping, spraying, extrusion, or insertion of the structure into the enclosure 10. An ovarian enclosure 10 may be implanted over the right ovary or the left ovary; separate enclosures 10 are used where both the right and left ovaries are enclosed. In some embodiments, it may be suitable to retain and enclose at least the left ovary in order to avoid confusion with appendicitis associated with right-side pain presentation.

The ovarian enclosure 10 may comprise additional features to aid in the detection of pathologic conditions affecting the ovaries, including ovarian cysts and ovarian cancer. As the enclosure 10 has a finite capacity to expand, abnormal growth of the ovary will assert pressure against the enclosure 10, causing localized pain in the area. The pain may, in turn, allow the patient to seek treatment of the condition earlier than she ordinarily might have sought treatment, especially if, absent the presence of the enclosure, the condition would remain asymptomatic, at least for some additional period of time. The pathological conditions aided by these additional features include, for example, dysplasia, pain, motility of the surface (hardening—oophosclerosis; softening—oophomalacia), and physical characteristics such as, for example, relative temperature, increased blood flow, and lesion identification.

To facilitate detection of an ovarian pathology, the enclosure 10 may comprise a plurality of fiducial markers 30 (see, FIG. 4A) that may be visualized via standard imaging techniques such as x-rays, ultrasound, magnetic resonance imaging, or tomography. If the enclosure 10 expands, the distance between fiducial markers 30 will expand, indicating to the practitioner that there may be a pathologic condition occurring with the ovary in the enclosure 10. Relatedly, the regionalization of expanded fiducial markers 30 may indicate the location of the pathology. The pathology may include one or more of inflammation, cysts, neoplasm, hyperplasia, hyperthecosis, or other ovarian growth or tumor, whether benign or malignant.

To facilitate detection of an ovarian pathology, the enclosure 10 may comprise a plurality of heat sensing markers 40 (see, FIG. 4B), which may be visualized via standard imaging techniques such as x-rays, ultrasound, magnetic resonance imaging, or tomography. The heat sensing markers 40 may, for example, comprise a thermal shape memory material such as nitinol, which would cause the markers 40 to expand or enlarge in the event of elevated heat, with the presence of heat indicating a pathology. In some embodiments, the heat sensing marker can be a thermister, a fiber optic, or graphene.

To facilitate detection of an ovarian pathology, the enclosure 10 may comprise one or more blood flow reflectors 50 (see, FIG. 4C), which may be used in connection with a flow meter that measures volume or velocity of blood flow into and/or out from the blood vessels that supply the ovary. Detection of blood volume or flow velocity may be used to detect the presence of an ovarian pathology.

Figure 5A:
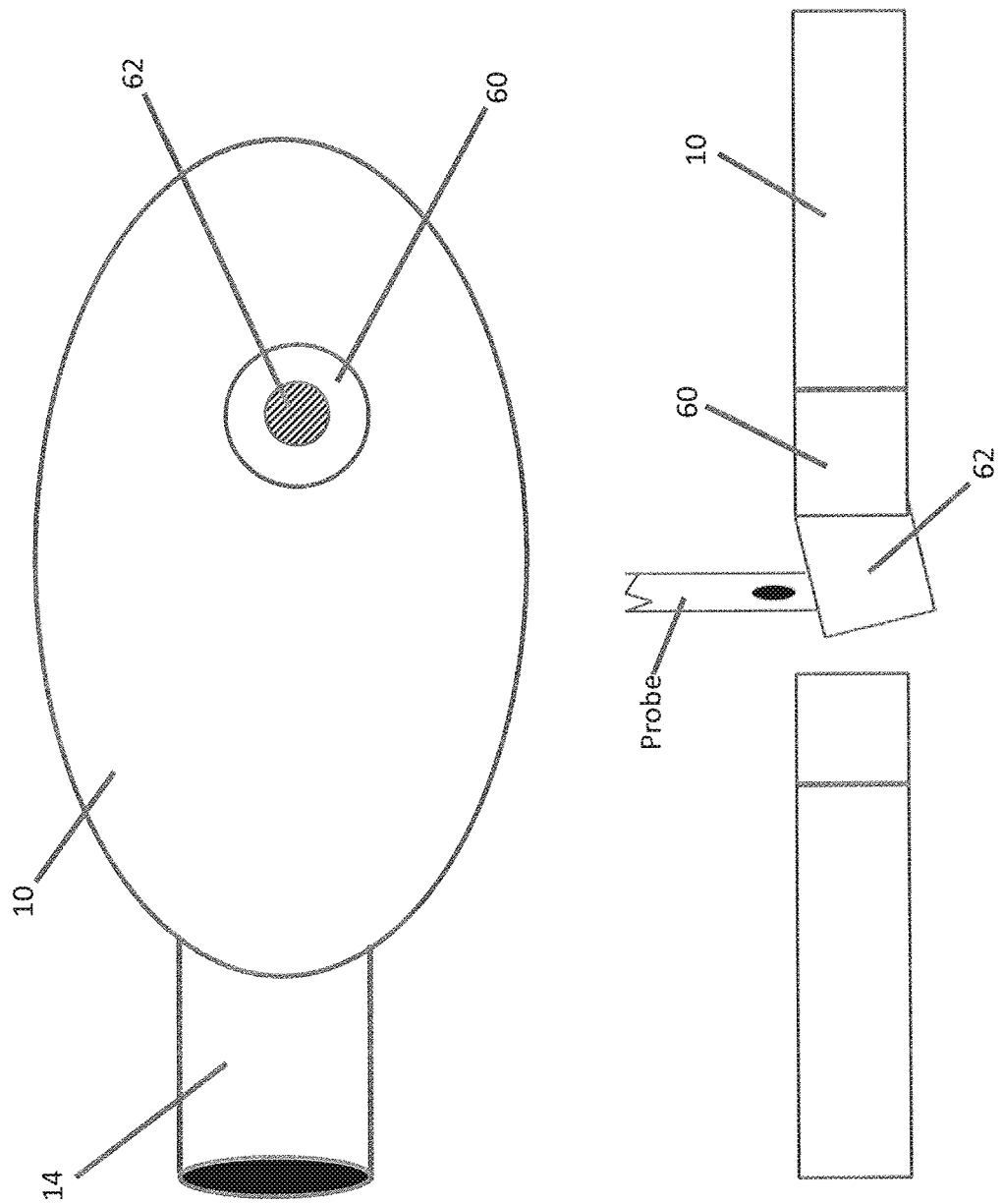
FIG. 5A shows an example of an ovarian enclosure with an access port.

In some embodiments, the enclosure 10 may comprise a port 60, which allows access to the internal contents of the enclosure 10 (see FIG. 5A; top drawing is a perspective view; bottom drawing is a partial cross-section view), or the trap lumen between the inner and outer layers of the enclosure 10. Access via the port 60 avoids the need to compromise the enclosure 10.

The port may further comprise a valve that closes the port but is capable of being opened when a probe presses the valve inward. The port may further comprise a seal or a sealant. The seal or sealant may comprise one or more of a biocompatible polymer, biocompatible gel, biocompatible wax, or biocompatible rubber such as a biocompatible silicone rubber. The port may further comprise one or more fiducial markers, one or more magnets, and/or one or more magnetic metals. The port may be operably connected to a tube that is also operably connected to the ovarian enclosure.

The port 60 may comprise a valve 62 that closes the port 60 when access is not desired. To gain access, an external probe such as a needle, tube, or catheter is inserted through the valve 62, from which ovarian tissue or other contents of the enclosure 10 may be aspirated or otherwise sampled/removed. In addition or in the alternate, the probe may be used to administer a therapeutic agent to treat a condition of the ovary (e.g., any ovarian condition described or exemplified herein) through the valve 62 port 60. Thus, the port 60 also allows for localized treatment of the ovary. The probe may, in some embodiments, insufflate the enclosure 10 via the valve 62, for example, to clear any debris that may block the probe or otherwise impede the probe's access or capacity to sample within the enclosure 10.

Figure 5B:
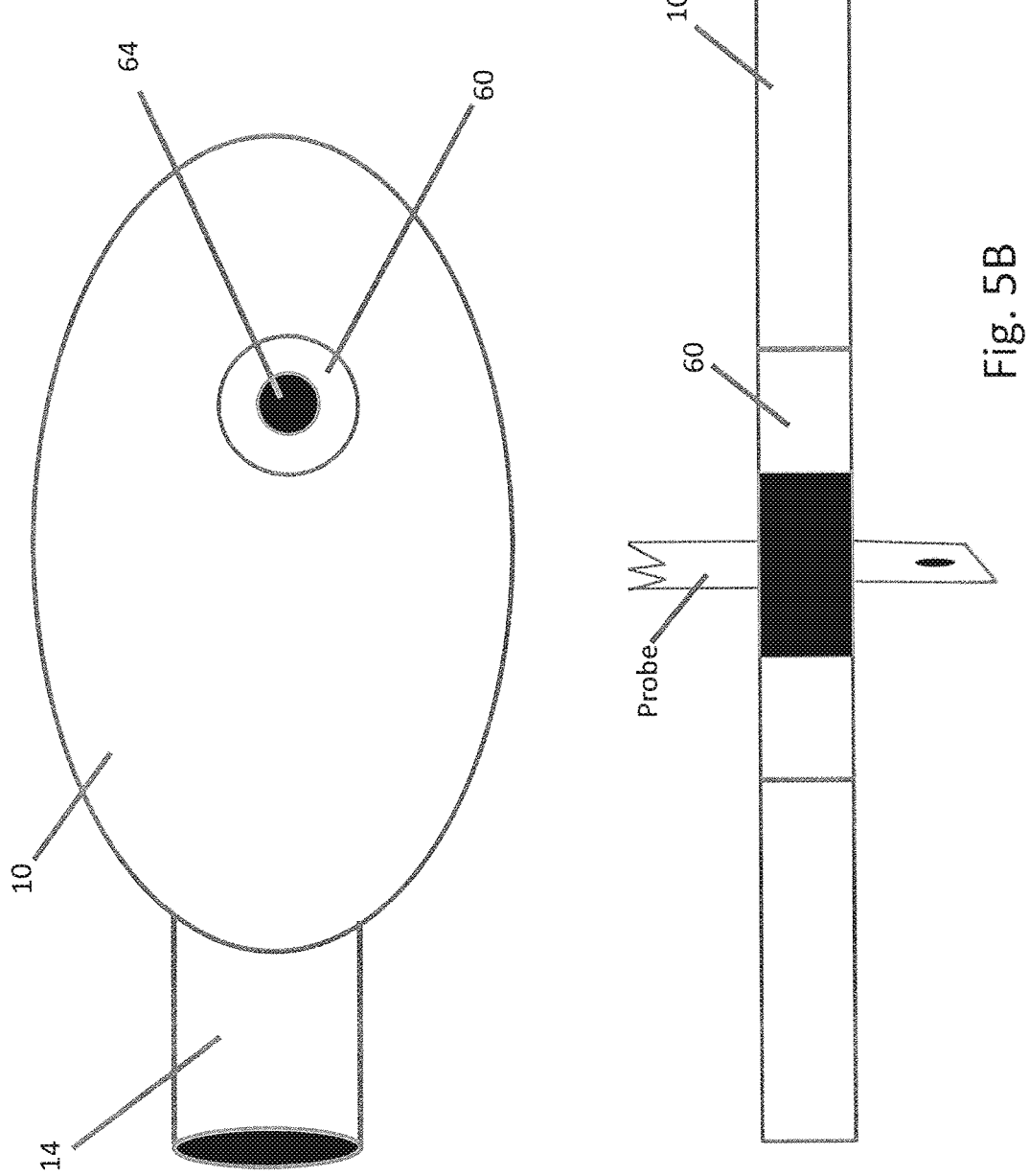
FIG. 5B shows an example of an ovarian enclosure with an access port and a seal or sealant.

In the alternate, or in addition to the valve 62, the port may further comprise a seal or sealant 64 through which the probe may be inserted (see, FIG. 5B; top drawings is a perspective view; the bottom drawing is a partial cross-section view). The seal or sealant 64 prevents escape of the enclosure 10 contents, including cancerous cells, in the event of valve 62 failure or by the puncture action of the probe (the seal or sealant 64 immediately closes around and off the probe while the probe is inserted, and the sealant recloses once the probe is removed). The seal or sealant 64 may comprise any suitable material, such as a biocompatible plastic, polymer, rubber, gel, wax, or silicone material.

Therapeutic agents to treat any condition of the ovary may be administered locally to the ovary through the sealant 64 and via the port 60. The probe may, in some embodiments, insufflate the enclosure 10 via the seal or sealant 64, for example, to clear any debris that may block the probe or otherwise impede the probe's access or capacity to sample within the enclosure 10. In some embodiments, the neck of the enclosure can be loosened to allow insertion of a biodegradeable chemotherapeutic eluting polymer construct. In some embodiments, the walls of the enclosure could be pierced or cut to allow insertion of an agent and patched following insertion.

Therapeutic agents that can be administered locally to the ovary may include biomolecules or chemical molecules, or combinations thereof. Categories of such agents include, but are not limited to, chemotherapeutic agents, anti-inflammatory agents, pain-relieving agents, and other agents suitable for the ovarian condition being treated. Suitable chemotherapeutic agents include, but are not limited to, Paclitaxel (Taxol®), albumin bound paclitaxel (nab-paclitaxel, Abraxane®), Altretamine (Hexalen®), Capecitabine (Xeloda®), Cyclophosphamide (Cytoxan®, Clafen®, Neosar®), Etoposide (VP-16), Gemcitabine (Gemzar®), Ifosfamide (Ifex®), Irinotecan (CPT-11, Camptosar®), Liposomal doxorubicin (Doxil®, Dox-SL®, Evacet®, LipoDox®) Alkeran (Melphalan), Pemetrexed (Alimta®), Topotecan (Hycamtin®), Vinorelbine (Navelbine®), Bevacizumab (Avastin®), Carboplatin, Cisplatin (Platinol®, Platinol-AQ®), Olaparib (Lynparza®), Carboplatin (Paraplat®, Paraplatin®), Rucaparib Camsylate (Rubraca®), and Thiotepa. In some embodiments, the chemotherapeutic agent is a combination of a platinum compound, such as cisplatin or carboplatin, and a taxane, such as paclitaxel (Taxol®) or docetaxel (Taxotere®). Other combinations include, but are not limited to, a combination of bleomycin, etoposide, cisplatin (BEP), Carboplatin-Taxol, Gemcitabine-Cisplatin, a combination of carboplatin (JM8), etoposide phosphate, and bleomycin sulfate (JEB), a combination of vincristine sulfate, dactinomycin (actinomycin-D), and cyclophosphamide (VAC), and a combination of vinblastine, ifosfamide and cisplatin (VeIP).

One advantage of treating an ovary with a therapeutic agent using the ovarian enclosure is that the therapeutic agent remains in close proximity to the ovary, and conversely, surrounding tissue is more apt to be protected from contact with the therapeutic agent. For example, the ovarian enclosure may affect therapeutic delivery of chemotherapeutic agents, such as Cisplatin, by keeping them in close proximity to the ovarian surface epithelium whilst protecting those agents from dissemination and dilution, and equally protecting proximal tissues from exposure to agents that may be harmful to those surrounding tissues.

In addition, the ovarian enclosure may be used to affix various diagnostic tools in close proximity to the epithelial surface of the ovary. For example, diagnostic biomarkers, such as HE4-9, EIA, and Urokinase Plasminogen Activator (u-PA) may have superior sensitivity and specificity to CA-125. Additional biomarkers include, but are not limited to: protein/antigen (e.g., CA-125, HE4, SMRP, OPN, VEGF, TTR, ApoA1, B7-H4, KLKs, PRSS8, M-CSF, LPA, IL-8, IL-6, OVX1, VCAM1, AGR-2, MMP-7, Serum Amyloid A), gene, DNA hypo/hyper-methylation (e.g., hypermethylated: BRCA1, p16, MLH1, RASSF1A, OPCML, LOT1, DAPK, PAR-4, ICAM-1, SPARC; hypomethylated: MCJ, SNCG, TRAG-3, IGF2, Claudin-4), histone modification (e.g., up-regulated: HDAC1-3, Rb, CDKN1; down-regulated: Class III b-tubulin, survivin, PACE4, Claudin-3, GATA4, GATA6), micro-RNA (e.g., up-regulated: miR-200a, miR-141, miR-200c, miR-200b, miR-203, miR-205; down-regulated: miR-199a, mIR-140, miR-145, miR-125b1, let-7i), and metabolites. These biomarkers may benefit from assured proximity and exclusive exposure to the ovarian surface.

The port 60 may be accessed surgically, for example, via a small incision. In some embodiments, the port 60 is accessed minimally invasively, for example, by inserting the probe directly through the skin and into the port 60. To this end, the fiducial markers 30 may indicate the location of the port 60 and, thus, assist in guiding the probe toward and into the port 60.

Figure 5C:
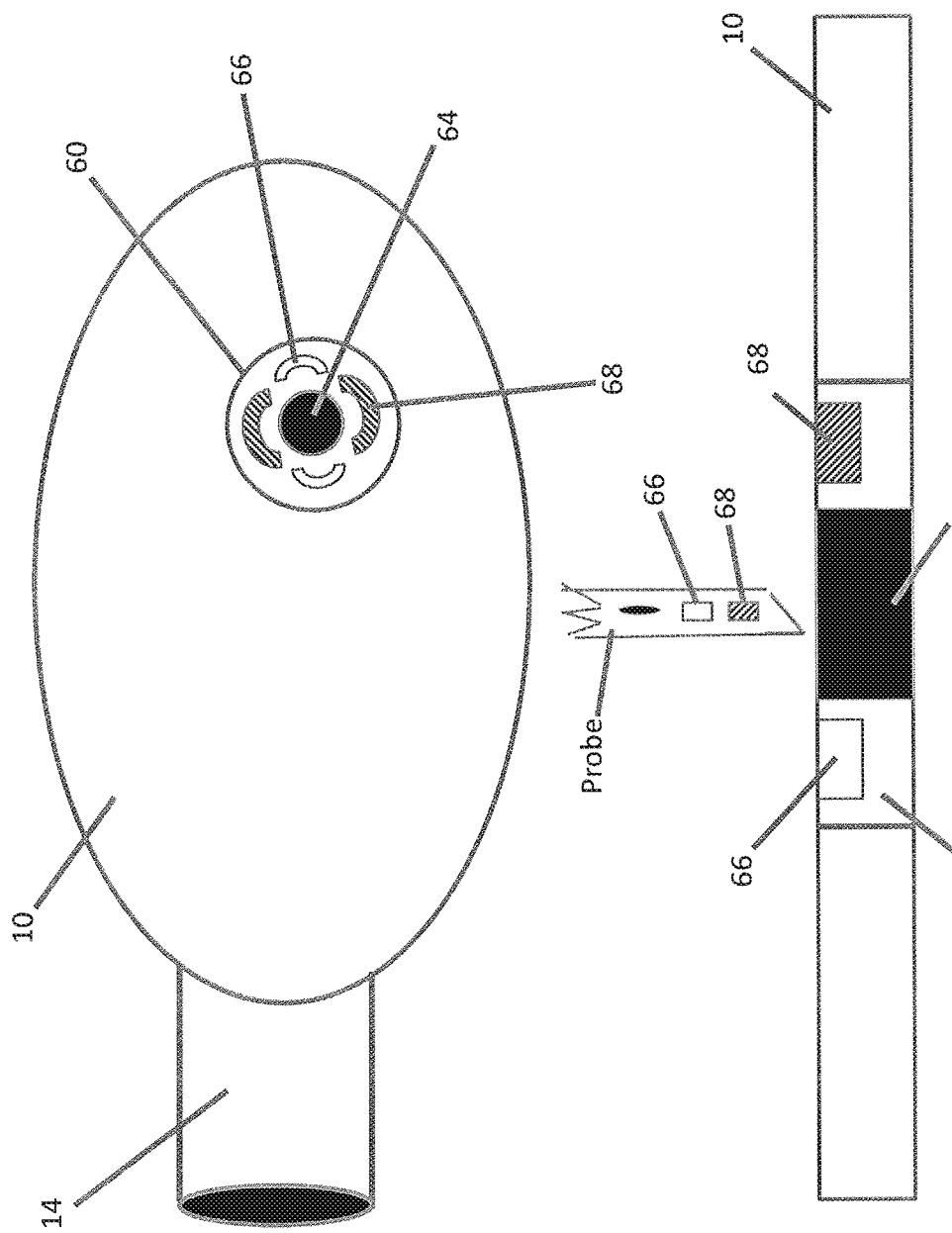
FIG. 5C shows an example of an ovarian enclosure with an access port and a magnet or magnetic material.

In addition or in the alternate to the fiducial markers 30, the port 60 may comprise a magnet 66 or magnetic metal 68 (see, FIG. 5C; the top drawing is a perspective view; the bottom drawing is a partial cross-section view). In such embodiments, the probe may include the cognate magnetic structure, such as a magnet when the port 60 comprises a magnetic metal 68, or such as a magnetic metal when the port 60 comprises a magnet 66. In this manner, the interaction of the magnet (66) and magnetic metal (68) on the port 60 and probe assist in guiding the probe toward and into the port 60.

In some embodiments, the port 60 may further be connected to a tube 70. For example, the tube 70 may be connected directly to the ovarian enclosure 10, with the port 60 located distally from the ovarian enclosure 10 (see, FIG. 6). This may permit less invasive access to the contents of the enclosure 10. For example, the tube 70 may extend into the vaginal canal, thus permitting the probe to be inserted into the vagina and into the port 60 within the vaginal canal, rather than puncturing the skin with the probe or with an incision to allow probe insertion into the body. Vaginal access also offers the additional advantage of avoiding the need for guided insertion as the port 60 should be visible to the practitioner. The tube 70 may be surgically fastened to the vaginal canal, for example, to avoid impeding intercourse or to avoid discomfort or to avoid feeling movement of the tube 70. For example, the tube may be fastened to a vaginal cuff established during the hysterectomy procedure. Alternately, the port 60 may be implanted at the body surface, for example, the navel, with the tube 70 extending through the body to the enclosure 10. In some embodiments, a body surface port 60 may also be covered by dermis to prevent external contamination.

In embodiments where the port 60 is located at a distal end of the tube 70 (opposite the end of the tube 70 connected to the enclosure 10), the port 60 may similarly comprise one or more of a valve 62, seal or sealant 64, magnet 66, or magnetic metal 68, as described above, to ensure that the integrity of the enclosure 10 is maintained, as well as to assist in accessing the port 60, even if the port 60 can otherwise be visualized without the need for imaging equipment.

The disclosure also provides methods for inhibiting the invasion of tissue adjacent to the organ by tumor cells. In some embodiments, the methods inhibit the invasion of tissue adjacent to the ovary by ovarian tumor cells. In general, the methods comprise implanting any embodiment of the organ enclosure, such as the ovarian enclosure 10 described or exemplified herein, into the body of the subject in need thereof. For example, the ovarian enclosure 10 is implanted by enclosing the ovary within the ovarian enclosure 10. In addition to the ovary, one or more of the suspensory ligament, the ovarian ligament, and the blood vessels (veins and/or arteries) that supply the ovary may be enclosed within the ovarian enclosure 10, for example, via the suspensory ligament sleeve 14, the ovarian ligament sleeve 16, and the one or more vasculature sleeves 18, which are sealed around their respective ligament or blood vessels.

The methods for inhibiting ovarian tumor cell invasion of tissue adjacent to the ovary generally comprises enclosing one or both ovaries in a subject in need thereof with any of the ovarian enclosures, including any features, described or exemplified herein. Enclosing one or both ovaries inhibits ovarian tumor cell invasion of tissue adjacent to one or both ovaries in the subject. Inhibiting ovarian tumor cell invasion may thus inhibit ovarian cancer metastasis. Where the enclosure comprises a suspensory ligament sleeve, the method may further comprise anchoring the suspensory ligament sleeve to the suspensory ligament connected to the ovary. Where the enclosure comprises an ovarian ligament sleeve, the method may further comprise anchoring the ovarian ligament sleeve to the ovarian ligament connected to the ovary. Where the enclosure comprises one or more blood vessel sleeves, the method may further comprise anchoring the one or more blood vessel sleeves to one or more blood vessels connected to the ovary. Such anchoring steps may be performed according to any technique suitable or desired by the medical practitioner, and may comprise one or more of gluing, suturing, clamping, or otherwise fastening the sleeve to the ligament or blood vessel, as the case may be.

The ovarian enclosures described herein may contain cancer progression if the ovary is already growing neoplasms at the time of hysterectomy. The ovarian enclosures described herein may deflect micro-migrations from the fallopian tubes.

An ovary may be enclosed, for example, during a hysterectomy procedure or other form of abdominal surgery. It is not necessary to enclose an ovary within the ovarian enclosure 10 as secondary to another surgery, as the enclosure 10 may be used in a stand-alone procedure, for example, in the event that the subject is determined to be at a heightened risk to develop ovarian cancer. In any case, either the left, right, or both ovaries may be enclosed.

The disclosure also provides methods for detecting a pathologic condition of an organ. In some embodiments, the methods provide detection of a pathologic condition of an ovary. In some embodiments, the methods comprise imaging one or more of the fiducial markers 30, the heat sensing markers 40, or the blood flow reflector 50 on an ovarian enclosure 10 implanted in the body of a subject. The imaging of the one or more of the fiducial markers 30, the heat sensing markers 40, or the blood flow reflector 50 may be according to any suitable imaging modality. A change in the location, spacing, or position of the fiducial markers 30 or the heat sensing markers 40 indicates an enlargement or bulge, or contraction at a particular portion of the ovarian enclosure 10 or of the ovarian enclosure 10 on the whole, thus indicating a change in the normal or healthy condition of the ovary. The pathologic condition may be benign or malignant. The pathologic condition may include ovarian atrophy, inflammation, cysts, neoplasm, hyperplasia, hyperthecosis, or other ovarian growth or tumor, whether the tumor is benign or malignant. The methods may further comprise treating the pathologic condition.

In some embodiments, a biomarker or other suitable marker that may be used to indicate a condition of the ovary may be incorporated or suspended within the enclosure 10. Such a marker may by detectable or sampled from the enclosure 10, for example, via the port 60. Such a marker may react with, for example, a cancerous condition to aid in the detection of such a condition.

In some embodiments, the methods comprise, or further comprise, sampling the internal contents of the ovarian enclosure. Sampling the contents may comprise inserting a probe, such as a needle or catheter, through the sidewalls of the ovarian enclosure 10, essentially compromising the enclosure. Alternately, sampling the contents may comprise inserting a probe, such as a needle or catheter, into the port 60 of the ovarian enclosure 60, which does not compromise the enclosure. The sampled contents may then be subject to further testing to determine the nature of the sampled contents, including whether or not the contents indicate that there is a change in the normal or healthy condition of the ovary, including the presence of a pathologic condition. The methods may further comprise treating the pathologic condition.

In some embodiments, a method for treating a pathologic condition of the ovary comprises detecting a change in the location, position, or spacing of the plurality of fiducial markers of the ovarian enclosure, and/or obtaining a sample of the internal contents of the ovarian enclosure, and then determining the type of pathologic condition of the ovary based on testing conducted on the sample, and then treating the pathologic condition. Obtaining a sample or the internal contents and/or treating the pathologic condition may comprise inserting a probe into the ovarian enclosure, for example, via a port in the enclosure. The probe may then be used to aspirate a sample of the enclosure contents, and/or administer a therapeutic agent locally to the ovary. If the condition is ovarian cancer, treating the cancer may comprise removing the cancerous ovary from the subject, or may comprise administering chemotherapeutic agents to the ovary, for example, via a port in the enclosure. If the condition is an ovarian cyst, treating the cyst may comprise removing the cyst or the ovary from the subject, or may comprise administering a cyst-treating therapeutic agent to the ovary, for example, via a port in the enclosure.

The ovarian enclosures described herein provide numerous advantages. First, the ovarian enclosures described herein will assist technicians in defining the ovarian surface through routine sonographic tools, deployed topically or intra-vaginally. By conforming to ovarian tissue and being compliant to its morphoses, the enclosures will provide fiducial markers to accurately convey any deviation from baseline size or shape of the ovary.

Although the ovary expands virtually painlessly, it is similar to the male testicle in its sensitivity to compression. In addition, although the ovarian implant will conform to and be compliant to the surface of the ovary, at some point its expansion will generate enough compression of ovarian tissue to cause pain. When the pain is great enough, the woman will seek clinical intervention. The implant will act as a constant and passive diagnostic tool to accelerate clinical presentation with pain, and increase the incidence of the clinical diagnosis of, early stage 1 ovarian cancer.

As a tumor matures within the ovary, it demands vastly greater resources than does healthy ovarian tissue. Accordingly, this change in metabolism may be detected through the relative temperature of the ovary in comparison to adjacent tissue. Once a base-line ratio is established, any deviation unrelated to ovulation may demand further inquiry. Blood flow is a corollary indication of unusual ovarian activity. Sensors may be placed to generate perfusion data to further assist doctors in making an accurate diagnosis.

Another advantage of using an organ enclosure is the possible avoidance of unnecessarily removing the organ itself.

The following representative embodiments are presented:

Embodiment 1. An enclosure comprising:

a biotextile, a medical textile, or both a biotextile and a medical textile;

a suspensory ligament sleeve, an ovarian ligament sleeve, or both a suspensory ligament sleeve and an ovarian ligament sleeve;

a plurality of fiducial markers; and an optional port for accessing the internal contents of the enclosure;

wherein the enclosure has an elasticity that allows the enclosure to expand in size; and wherein the biotextile, medical textile, or both the biotextile and the medical textile inhibit the passage of live ovarian cells out from the enclosure.

Embodiment 2. The enclosure according to embodiment 1, wherein the biotextile comprises xenograft extracellular matrix.

Embodiment 3. The enclosure according to embodiment 1 or 2, wherein the medical textile comprises polypropylene, polyethylene, polyvinyl chloride, polyurethane, polyethylene terephthalate, poly-L-lactide, poly-DL-lactide, polyglycolic acid, poly(lactic-co-glycolic acid), polydioxanone, polytetrafluoroethylene, or nylon, or any copolymer thereof.

Embodiment 4. The enclosure according to any one of embodiments 1 to 3, wherein the medical textile comprises polypropylene.

Embodiment 5. The enclosure according to any one of embodiments 1 to 3, wherein the medical textile comprises polytetrafluoroethylene.

Embodiment 6. The enclosure according to embodiment 1 or 2, wherein the medical textile comprises a silicone rubber.

Embodiment 7. The enclosure according to embodiment 1 or 2, wherein the medical textile comprises a neoprene rubber.

Embodiment 8. The enclosure according to any one of embodiments 1 to 7, wherein the biotextile or the medical textile comprises a biocompatible film.

Embodiment 9. The enclosure according to any one of embodiments 1 to 8, wherein the enclosure comprises a plurality of layers.

Embodiment 10. The enclosure according to embodiment 9, wherein the enclosure comprises an outer layer and an inner layer, and a space between the outer layer and the inner layer capable of trapping live ovarian cells.

Embodiment 11. The enclosure according to any one of embodiments 1 to 10, wherein the biotextile or the medical textile have an elasticity that allows the enclosure to expand up to about 50% in size.

Embodiment 12. The enclosure according to any one of embodiments 1 to 11, wherein the biotextile or the medical textile have an elasticity that allows the enclosure to expand up to about 33% in size.

Embodiment 13. The enclosure according to any one of embodiments 1 to 12, wherein the biotextile or the medical textile have an elasticity that allows the enclosure to expand up to about 25% in size.

Embodiment 14. The enclosure according to any one of embodiments 1 to 13, wherein the biotextile or the medical textile have an elasticity that allows the enclosure to expand up to about 10% in size.

Embodiment 15. The enclosure according to any one of embodiments 1 to 14, wherein the enclosure comprises a suspensory ligament sleeve, but not an ovarian ligament sleeve.

Embodiment 16. The enclosure according to any one of embodiments 1 to 15, further comprising one or more blood vessel sleeves.

Embodiment 17. The enclosure according to any one of embodiments 1 to 16, further comprising a first clamp for securing the suspensory ligament sleeve to the suspensory ligament connected to the ovary.

Embodiment 18. The enclosure according to any one of embodiments 1 to 17, further comprising one or more second clamps for securing the one or more blood vessel sleeves to blood vessels connected to the ovary.

Embodiment 19. The enclosure according to any one of embodiments 1 to 14, further comprising a first clamp for securing the suspensory ligament sleeve to the suspensory ligament connected to the ovary, and a third clamp for securing the ovarian ligament sleeve to the ovarian ligament connected to the ovary.

Embodiment 20. The enclosure according to embodiment 19, further comprising one or more second clamps for securing the one or more blood vessel sleeves to blood vessels connected to the ovary.

Embodiment 21. The enclosure according to any one of embodiments 17 to 20, wherein the first clamp comprises a hinge, a first end, and a second end, and the first end and second end are capable of locking together.

Embodiment 22. The enclosure according to embodiment 18 or 20, wherein the one or more second clamps comprise a hinge, a first end, and a second end, and the first end and second end are capable of locking together.

Embodiment 23. The enclosure according to embodiment 19 or 20, wherein the third clamp comprises a hinge, a first end, and a second end, and the first end and second end are capable of locking together.

Embodiment 24. The enclosure according to any one of embodiments 1 to 23, further comprising one or more heat sensing markers.

Embodiment 25. The enclosure according to any one of embodiments 1 to 24, further comprising a blood flow reflector.

Embodiment 26. The enclosure according to any one of embodiments 1 to 25, wherein the port further comprises a valve that closes the port but is capable of being opened when a probe presses the valve inward.

Embodiment 27. The enclosure according to any one of embodiments 1 to 26, wherein the port further comprises a seal or a sealant.

Embodiment 28. The enclosure according to embodiment 27, wherein the seal or sealant comprises a biocompatible polymer.

Embodiment 29. The enclosure according to embodiment 27, wherein the seal or sealant comprises a biocompatible gel.

Embodiment 30. The enclosure according to embodiment 27, wherein the seal or sealant comprises a biocompatible wax.

Embodiment 31. The enclosure according to embodiment 27, wherein the seal or sealant comprises a biocompatible rubber.

Embodiment 32. The enclosure according to embodiment 31, wherein the biocompatible rubber comprises silicone.

Embodiment 33. The enclosure according to any one of embodiments 1 to 32, wherein the enclosure further comprises one or more fiducial markers.

Embodiment 34. The enclosure according to any one of embodiments 1 to 33, wherein the port further comprises a magnet.

Embodiment 35. The enclosure according to any one of embodiments 1 to 33, wherein the port further comprises a magnetic metal.

Embodiment 36. The enclosure according to any one of embodiments 1 to 35, wherein the port is operably connected to a tube that is also operably connected to the ovarian enclosure.

Embodiment 37. The enclosure according to any one of embodiments 1 to 36, wherein the fiducial markers are capable of being visualized by ultrasonic imaging.

Embodiment 38. The enclosure according to any one of embodiments 1 to 37, wherein the fiducial markers are capable of being visualized by magnetic resonance imaging.

Embodiment 39. The enclosure according to any one of embodiments 1 to 38, wherein the fiducial markers are capable of being visualized by radiographic imaging.

Embodiment 40. The enclosure according to embodiment 39, wherein the radiographic imaging comprises tomography.

Embodiment 41. The enclosure according to any one of embodiments 1 to 40, wherein the biotextile is anti-adhesive, non-immunogenic, and does not promote cellular invasion or vascularization of the biotextile.

Embodiment 42. The enclosure according to any one of embodiments 1 to 41, wherein the medical textile is anti-adhesive.

Embodiment 43. The enclosure according to any one of embodiments 1 to 42, wherein ovarian cells comprise ovarian cancer cells.

Embodiment 44. A method for inhibiting ovarian tumor cell invasion of tissue adjacent to the ovary, comprising enclosing one or both ovaries in a subject in need thereof with the enclosure according to any one of embodiments 1 to 43, thereby inhibiting ovarian tumor cell invasion of tissue adjacent to one or both ovaries in the subject.

Embodiment 45. The method according to embodiment 44, wherein the method further comprises anchoring the suspensory ligament sleeve to the suspensory ligament connected to the ovary by suturing the suspensory ligament sleeve to said suspensory ligament.

Embodiment 46. The method according to embodiment 44, wherein the method further comprises anchoring the suspensory ligament sleeve to the suspensory ligament connected to the ovary by gluing the suspensory ligament sleeve to said suspensory ligament.

Embodiment 47. The method according to embodiment 44, wherein the method further comprises anchoring the ovarian ligament sleeve to the ovarian ligament connected to the ovary by suturing the ovarian ligament sleeve to said ovarian ligament.

Embodiment 48. The method according to embodiment 44, wherein the method further comprises anchoring the ovarian ligament sleeve to the ovarian ligament connected to the ovary by gluing the ovarian ligament sleeve to said ovarian ligament.

Embodiment 49. The method according to embodiment 44, wherein the method further comprises anchoring the one or more blood vessel sleeves to one or more blood vessels connected to the ovary by suturing the one or more blood vessels sleeves to said one or more blood vessels.

Embodiment 50. The method according to embodiment 44, wherein the method further comprises anchoring the one or more blood vessel sleeves to one or more blood vessels connected to the ovary by gluing the one or more blood vessels sleeves to said one or more blood vessels.

Embodiment 51. The method according to any one of embodiments 44 to 50, wherein the subject is a human being.

Embodiment 52. A method for treating a pathologic condition of the ovary, comprising detecting a change in the location, position, or spacing of the plurality of fiducial markers of the enclosure according to any one of embodiments 1 to 43 which has been implanted in the body of a subject, obtaining a sample of the internal contents of the enclosure and determining the type of pathologic condition of the ovary based on testing conducted on the sample, and treating the pathologic condition.

Embodiment 53. The method according to embodiment 52, wherein obtaining a sample comprises inserting a probe into the enclosure and aspirating the sample.

Embodiment 54. The method according to embodiment 53, wherein the probe is inserted into the port.

Embodiment 55. The method according to any one of embodiments 52 to 54, where treating the pathologic condition comprises administering a therapeutic agent locally to the ovary via a port in the enclosure.

Embodiment 56. The method according to any one of embodiments 52 to 54 wherein the pathologic condition is ovarian cancer and treating the pathologic condition comprises removing one or both of ovaries from the subject.

Embodiment 57. The method according to any one of embodiments 52 to 54, wherein the pathologic condition is ovarian cysts and treating the pathologic condition comprises removing the ovarian cysts from one or both of ovaries of the subject.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Partial Enclosure—Ophidian Spiral Thread of Silicon

In one embodiment, the ovarian enclosure is an ophidian spiral thread of silicon that may enhance the clinician's efforts to image the ovarian surface. This structure may be held in place by friction, glue or a simple fastening method such as a suture placed at one or more locations to avoid future motility of the ovarian enclosure.

Example 2: Complete Enclosure

A complete containment of the ovarian surface can be accomplished with a very thin silicon enclosure, applied much like unrolling a condom. Silicon may add to the opacity of the ovary to aid ovarian surface imaging, but should elements such as metallic particulates need to be added to the silicon to enhance its opacity, it must adhere to and conform to the surface of the ovary. This structure may be held in place by friction, glue or a simple fastening method such as a suture placed at one or more locations to avoid future motility of the ovarian enclosure.

Example 3: Multiple Layered Ovarian Enclosure

In another embodiment, the ovarian enclosure involves multiple layers of materials, each designed to perform a specific task. The outer layer may serve the purpose of an anti-adhesive or anti-microbial layer to prevent immediate post-surgical complications. This outer layer may be constructed of hyaluronic acid, Rifampin impregnated Tyrosine, or other agents approved for internal use that may eventually break down through hydrolysis.

The inner layer(s) may include a thin silicon layer to aid in imaging as described above, and an inner layer or layers of material, such as polyesters with varying weave porosity designed to impede ovarian expansion beyond a certain multiple of base-line size, or contain cellular migrations between various layers.

This enclosure may be wrapped around the ovary and set with various biocompatible glues such as Cohera Medical's TissuGlu.

The disclosure is not limited to the embodiments described and exemplified above, but is capable of variation and modification within the scope of the appended claims.

What is claimed is:

1. A permanently implantable ovarian enclosure, comprising:
    a body configured to enclose an ovary;
    a suspensory ligament sleeve and an ovarian ligament sleeve, each extending from said body of the ovarian enclosure;
    a first fixation element configured for securing the suspensory ligament sleeve to a suspensory ligament connected to an ovary;
    a second fixation element configured for securing the ovarian ligament sleeve to an ovarian ligament connected to the ovary; and
    a plurality of fiducial markers at spaced locations on said body of the ovarian enclosure;
    wherein the ovarian enclosure is made of a biotextile, a medical textile, or a combination of both a biotextile and medical textile, wherein the biotextile, the medical textile or the combination of both the biotextile and medical textile is configured to inhibit the passage of pathological live ovarian cells or cyst fluid out from the ovarian enclosure;
    wherein the ovarian enclosure has an elasticity configured to cease expansion of the body of the ovarian enclosure at a predetermined volume relative to a volume of the body of the ovarian enclosure at implantation; and
    a tube connected to the body of the ovarian enclosure and extending therefrom, the tube including a first end connected directly to the body of the ovarian enclosure and a second end configured to extend remotely from the body, wherein the second end of the tube has a normally-closed valve, seal, or sealant; and
    wherein the enclosure has an elasticity that allows the enclosure to expand up to 10%, up to 25%, up to 33%, or up to 50% in size of ovarian volume at implantation.

2. The enclosure according to claim 1, wherein the enclosure comprises the biotextile, and the biotextile comprises xenograft extracellular matrix.

3. The enclosure according to claim 1, wherein the enclosure comprises the medical textile, and the medical textile comprises polypropylene, polyethylene, polyvinyl chloride, polyurethane, polyethylene terephthalate, poly-L-lactide, poly-DL-lactide, polyglycolic acid, poly(lactic-co-glycolic acid), polydioxanone, polytetrafluoroethylene, or nylon, or any copolymer thereof.

4. The enclosure according to claim 1, wherein the enclosure comprises the medical textile, and the medical textile comprises a silicone rubber or a neoprene rubber.

5. The enclosure according to claim 1, wherein the biotextile or the medical textile comprises a biocompatible film.

6. The enclosure according to claim 1, wherein the enclosure comprises a plurality of layers.

7. The enclosure according to claim 1, further comprising one or more blood vessel sleeves.

8. The enclosure according to claim 7, further comprising one or more clamps for securing the one or more blood vessel sleeves to blood vessels connected to the ovary.

9. The enclosure according to claim 1, wherein the first fixation element is a clamp for securing the suspensory ligament sleeve to the suspensory ligament connected to the ovary; and wherein the second fixation element is a clamp for securing the ovarian ligament sleeve to the ovarian ligament connected to the ovary.

10. The enclosure according to claim 9, wherein each clamp comprises a hinge, a first end, and a second end, and the first end and second end are configured for locking together.

11. The enclosure according to claim 1, further comprising one or more heat sensing markers and/or a blood flow reflector.

12. The enclosure according to claim 1, wherein the fiducial markers are configured for being visualized by ultrasonic imaging, magnetic resonance imaging, or radiographic imaging.

13. The enclosure according to claim 1, wherein the enclosure comprises the biotextile, and the biotextile is anti-adhesive and non-immunogenic.

14. The enclosure according to claim 1, wherein the enclosure comprises the medical textile, and the medical textile is anti-adhesive.

15. A method for inhibiting ovarian tumor cell invasion of tissue adjacent to the ovary, comprising enclosing one or both ovaries in a subject in need thereof within the enclosure according to claim 1, said enclosure inhibiting the ovarian tumor cell invasion of tissue adjacent to one or both ovaries in the subject.

16. A method for treating a pathologic condition of the ovary, comprising detecting a change in the location, position, or spacing of the plurality of fiducial markers of the enclosure according to claim 1 which has been implanted in the body of a subject, obtaining a sample of internal contents of the enclosure, determining the type of pathologic condition of the ovary based on testing conducted on the sample, and treating the pathologic condition.

17. The method according to claim 16, wherein treating the pathologic condition comprises administering a therapeutic agent locally to the ovary.

18. The method according to claim 16, wherein the pathologic condition is ovarian cancer, and treating the ovarian cancer comprises removing the one or both of ovaries from the subject or wherein the pathologic condition is ovarian cysts, and treating the ovarian cysts comprises removing the ovarian cysts from the one or both of ovaries of the subject.

19. The method of claim 16, wherein said pathological condition is selected from ovarian atrophy, ovarian inflammation, ovarian dysplasia, oophosclerosis, oophomalacia, ovarian cysts, malignant ovarian neoplasms, benign ovarian tumors, ovarian hyperplasia, and hyperthecosis.

20. The method of claim 16, wherein the detection steps include determining expansion of said enclosure and assessing pain levels in said subject, wherein said pain is caused by pathology induced expansion of the ovary.

* * * * *